(12) United States Patent
Congdon et al.

(10) Patent No.: US 12,201,785 B2
(45) Date of Patent: Jan. 21, 2025

(54) ENDOSCOPIC MEDICAL DEVICE AND METHOD OF USE

(71) Applicant: Boston Scientific Scimed, Inc., Maple Grove, MN (US)

(72) Inventors: Daniel Congdon, Pepperell, MA (US); Laurie A. Lehtinen, Boylston, MA (US); Shawn Ryan, Littleton, MA (US); Joseph W. King, Franklin, MA (US)

(73) Assignee: Boston Scientific Seimed, Inc., Maple Grove, MN (US)

( * ) Notice: Subject to any disclaimer, the term of this patent is extended or adjusted under 35 U.S.C. 154(b) by 144 days.

(21) Appl. No.: 17/986,946

(22) Filed: Nov. 15, 2022

(65) Prior Publication Data

US 2023/0076237 A1 Mar. 9, 2023

Related U.S. Application Data

(62) Division of application No. 16/916,856, filed on Jun. 30, 2020, now Pat. No. 11,524,141.

(60) Provisional application No. 62/871,422, filed on Jul. 8, 2019.

(51) Int. Cl.
*A61M 25/01* (2006.01)
*A61M 25/00* (2006.01)
*A61M 25/02* (2006.01)

(52) U.S. Cl.
CPC .... *A61M 25/0113* (2013.01); *A61M 25/0136* (2013.01); *A61M 25/0147* (2013.01); *A61M 2025/0019* (2013.01); *A61M 2025/024* (2013.01)

(58) Field of Classification Search
CPC .............. A61B 17/128; A61B 17/1285; A61B 2090/0803; A61B 2090/0814; A61B 2017/00367; A61B 90/03; A61M 25/0113; A61M 25/0136; A61M 25/0147; A61M 2025/024
See application file for complete search history.

(56) References Cited

U.S. PATENT DOCUMENTS

| | | | |
|---|---|---|---|
| 3,958,576 | A | 5/1976 | Komiya et al. |
| 5,084,057 | A | 1/1992 | Green et al. |
| 5,487,499 | A | 1/1996 | Sorrentino et al. |
| 5,766,184 | A | 6/1998 | Matsuno |
| 6,210,398 | B1 | 4/2001 | Ouchi |

(Continued)

FOREIGN PATENT DOCUMENTS

DE 29505619 U1 6/1995

*Primary Examiner* — Nathan R Price
*Assistant Examiner* — John A Doubrava
(74) *Attorney, Agent, or Firm* — Bookoff McAndrews, PLLC

(57) ABSTRACT

A medical device including a handle body having a proximal end and a distal end, a spool on the handle body and to move between the distal end and the proximal end of the handle body, a catheter extending from the distal end of the handle body, an actuator attached to the spool and extending through the catheter, such that the actuator is removably connected to one or more dispensable devices at a distal end of the catheter, a spool controller to prevent connection with another of the dispensable devices to the actuator after a predetermined number of dispensable devices have been dispensed by the medical device.

17 Claims, 8 Drawing Sheets

(56) References Cited

U.S. PATENT DOCUMENTS

| | | |
|---|---|---|
| 6,423,079 B1 | 7/2002 | Blake, III |
| 6,773,438 B1 | 8/2004 | Knodel et al. |
| 6,814,742 B2 | 11/2004 | Kimura et al. |
| 8,496,673 B2 | 7/2013 | Nguyen et al. |
| 9,968,363 B2 | 5/2018 | Blake, III |
| 11,524,141 B2 * | 12/2022 | Congdon ............ A61M 25/0113 |
| 2006/0190015 A1 * | 8/2006 | Matsuno .............. A61B 17/122 |
| | | 606/142 |
| 2008/0306491 A1 | 12/2008 | Cohen et al. |
| 2018/0263624 A1 | 9/2018 | Malkowski et al. |
| 2019/0090882 A1 | 3/2019 | Estevez et al. |

\* cited by examiner

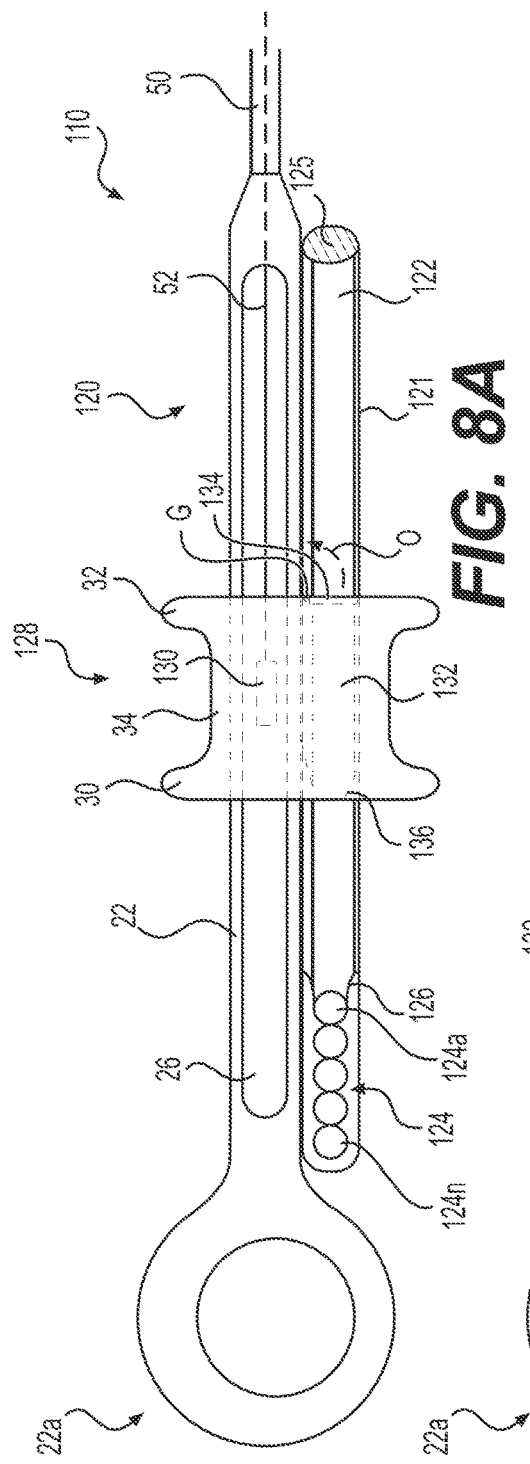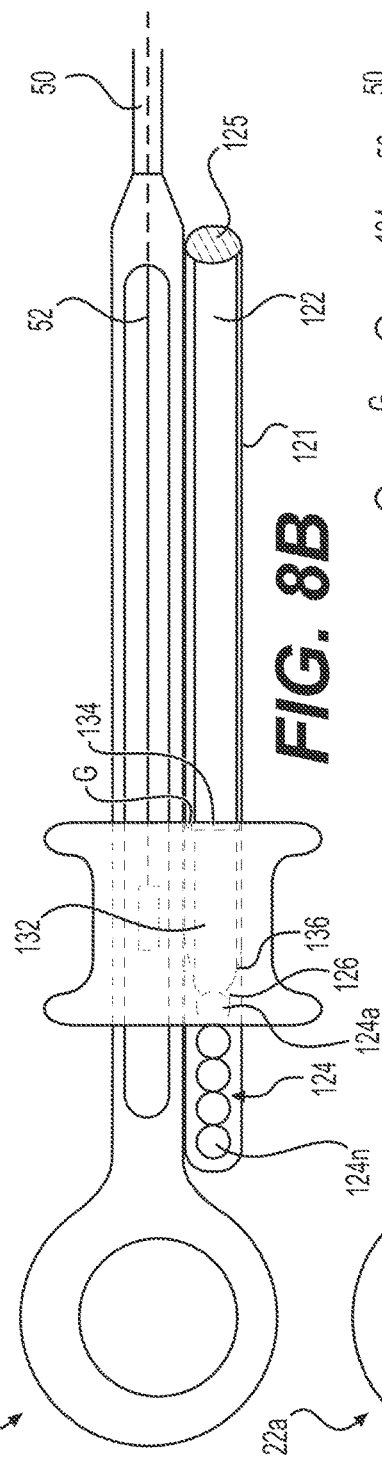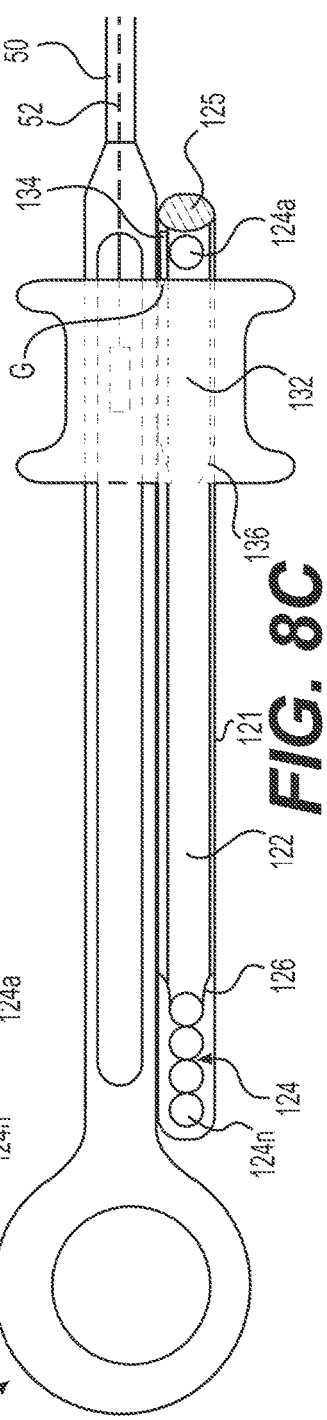

ENDOSCOPIC MEDICAL DEVICE AND METHOD OF USE

CROSS-REFERENCE TO RELATED APPLICATIONS

This application is a divisional of U.S. application Ser. No. 16/916,856, filed on Jun. 30, 2020, which claims the benefit of priority from U.S. Provisional Application No. 62/871,422, filed Jul. 8, 2019, which are incorporated by reference herein in their entireties.

TECHNICAL FIELD

The present disclosure relates generally to endoscopic medical devices and methods of use. More particularly, in some embodiments, the disclosure relates to tools, systems, and/or methods for dispensing one or more devices to a target site in a patient for, e.g., fixing or fastening tissue or performing any other diagnostic or therapeutic procedure.

BACKGROUND

Conventional endoscope devices for dispensing one or more devices in a patient are sometimes provided as single-use devices. These single-use devices are intended to carry a predetermined number of dispensable devices, e.g., tissue clips, and may not be designed as a reloadable/reusable system. Sterilization of these endoscope devices can be difficult, and failure to properly sterilize these devices can be harmful to patients by, e.g., spreading disease. Further, multiple uses of these single-use devices may increase a patient risk of disease or infection and/or may increase a risk of device failure.

The present disclosure may solve one or more of these problems or other problems in the art. The scope of the disclosure, however, is defined by the attached claims and not the ability to solve a specific problem.

SUMMARY OF THE DISCLOSURE

According to an example, a medical device including a handle body having a proximal end and a distal end, a spool on the handle body and to move between the distal end and the proximal end of the handle body, a catheter extending from the distal end of the handle body, an actuator attached to the spool and extending through the catheter, such that the actuator is removably connected to one or more dispensable devices at a distal end of the catheter, a spool controller to prevent connection with another of the dispensable devices to the actuator after a predetermined number of dispensable devices have been dispensed by the medical device.

The spool controller may include a ratchet disposed about the handle body, the ratchet may include a plurality of distally facing cavities, and a final cavity from the plurality of cavities may have a configuration different from the other plurality of cavities.

The spool may include a proximally facing protrusion, and the protrusion may be configured to sequentially and individually enter each of the plurality of distally facing cavities.

A distal facing surface of the protrusion may engage with a proximal facing surface of the final cavity to lock the spool on the handle body.

The ratchet may rotate about the handle body when the protrusion enters each of the plurality of cavities.

Each of the plurality of cavities may include a wall sloped relative to a longitudinal axis of the medical device, and contacting the wall with the protrusion may cause the ratchet to rotate about the handle body.

The protrusion may be configured to enter the final cavity and lock the spool at the proximal end of the handle.

The spool controller may include a handle chamber extending along the handle body, and a spool chamber defined by the spool, such that the spool chamber may be movable within the handle chamber.

The medical device may include a plurality of elements disposed within the handle chamber, the plurality of elements may be configured to be moved sequentially and individually from a proximal end of the handle chamber to a distal end of the handle chamber.

The handle chamber may further include a magnet at a distal end, and a magnetic force of the magnet may be configured to pull at least one of the plurality of the elements from the spool chamber toward the distal end of the handle chamber.

The spool chamber may release a distalmost element from the plurality of elements at the proximal end of the handle chamber and moves the distalmost element toward the distal end of the handle chamber.

A distal end of the spool chamber may include a gate, and the gate may be biased in a closed configuration closing the distal end of the spool chamber.

The magnet may overcome a bias of the gate to pull at least one of the plurality of elements through the gate toward the magnet.

A distal end of the actuator may extend at least a predetermined distance from a distalmost end of the catheter to attach to one of the plurality of dispensable devices.

A dispensable device of the plurality of dispensable devices may be incapable of attaching to the distal end of the actuator when the plurality of elements at the distal end of handle chamber extend a distance greater than the predetermined distance.

According to another example, a medical device includes a handle body having a distal end and a proximal end, a spool on the handle body and movable between the distal and proximal ends, the spool including a protrusion extending toward the proximal end of the handle body, a catheter extending from the distal end of the handle body, an actuator attached to the spool and extending through the catheter, the actuator configured to be removably connected to a dispensable device at a distal end of the catheter, and a ratchet disposed about the handle body and proximal to the spool, the ratchet includes a cavity, the protrusion is configured to enter the cavity and cause rotation of the ratchet when the dispensable device is dispensed from the medical device.

The protrusion may protrude from a proximal surface of the spool.

The protrusion may lock the spool to the ratchet mechanism after the dispensable device has been dispensed.

According to yet another example, a medical device, includes a handle body having a distal end, a proximal end, and a handle chamber extending along a length of the handle body, a spool on the handle body and movable between the distal and the proximal ends, the spool including a spool chamber movable within the handle chamber, a catheter extending from the distal end of the handle body, and an actuator attached to the spool and extending through the catheter, the actuator is configured to be removably connected to a first dispensable device at a distal end of the catheter, the handle chamber includes at least one element, and the medical device prevents loading of a second dispensable device when the at least one element is disposed at a distal end of the handle chamber.

A distal end of the actuator extends at least a predetermined distance from a distalmost end of the catheter to attach the second dispensable device, and the second dispensable device may be incapable of attaching to the distal end of the actuator when at least one element at the distal end of the handle chamber extends a distance greater than the predetermined distance from the distal end of the handle chamber.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 8A-8C are side views of a medical device according to another embodiment.

DETAILED DESCRIPTION

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Figure 1:
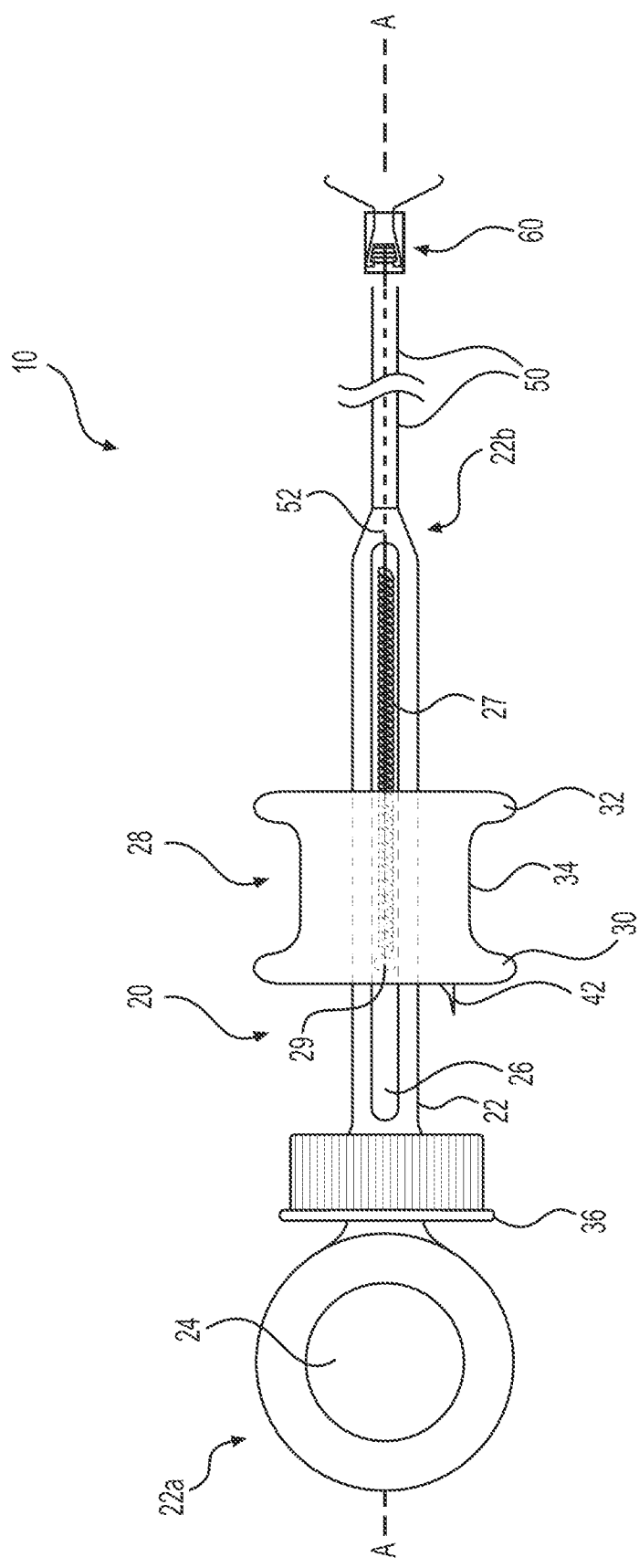
FIG. 1 is a side of a medical device according to an exemplary embodiment.

As described above, single-use devices should be used in a single procedure to reduce or minimize the transmission of disease and infection. Repurposed dispensing devices may be improperly loaded with improperly structured or sized dispensable devices, e.g., tissue clips. Systems and devices according to exemplary embodiments of the present disclosure may be limited to pre-loaded dispensable devices, e.g., devices may not be reloaded for subsequent use. Dispensable devices may be pre-loaded for a single procedure, for example, a plurality of clips may be dispensed for a tissue closure procedure. Referring to FIG. 1, a medical device 10 (e.g., a device for dispensing devices, such as medical clips) according to an embodiment is shown. Medical device 10 includes a handle 20, a catheter 50 connected to handle 20, and one or more dispensable devices 60 (e.g., a clip for fastening tissue) at a distal end of catheter 50, opposite handle 20.

With continued reference to FIG. 1, handle 20 is illustrated. Handle 20 includes a body 22 defining a hole 24 in body 22 at a proximal end 22a thereof. Hole 24 can be used to accommodate a thumb of a user of device 10. Catheter 50 is attached at an opposite, distal end 22b of body 22. A slot 26 extends through body 22 in a direction parallel to a longitudinal axis A of catheter 50. A spool 28 includes a bar 29 disposed in slot 26, and bar 29 moves within slot 26 and along body 22 in a direction parallel to longitudinal axis A. A spring 27 extends within slot 26 from a distalmost end of bar 29 to a distalmost end of slot 26. Spring 27 is biased to pull bar 29 and spool 28 distally to load a device, as will be described herein. A wire 52 (or any other elongate actuator, such as a cable, a braided member, etc.) extends from the distal end of bar 29 distally through catheter 50 and to dispensable device 60. As will be described herein, actuation of spool 28 in a proximal direction relative to body 22 causes wire 52 to actuate and release dispensable device 60.

As further shown in FIG. 1, spool 28 includes two annular protrusions 30, 32 at a distal end and a proximal end thereof, respectively, and extending from spool 28 in a direction perpendicular to the direction of longitudinal axis A and the extension of catheter 50. Annular protrusions 30, 32 define an annular grip 34, which is grasped by a user (e.g., by a middle finger and an index finger) as will be described in greater detail herein.

Figure 2:
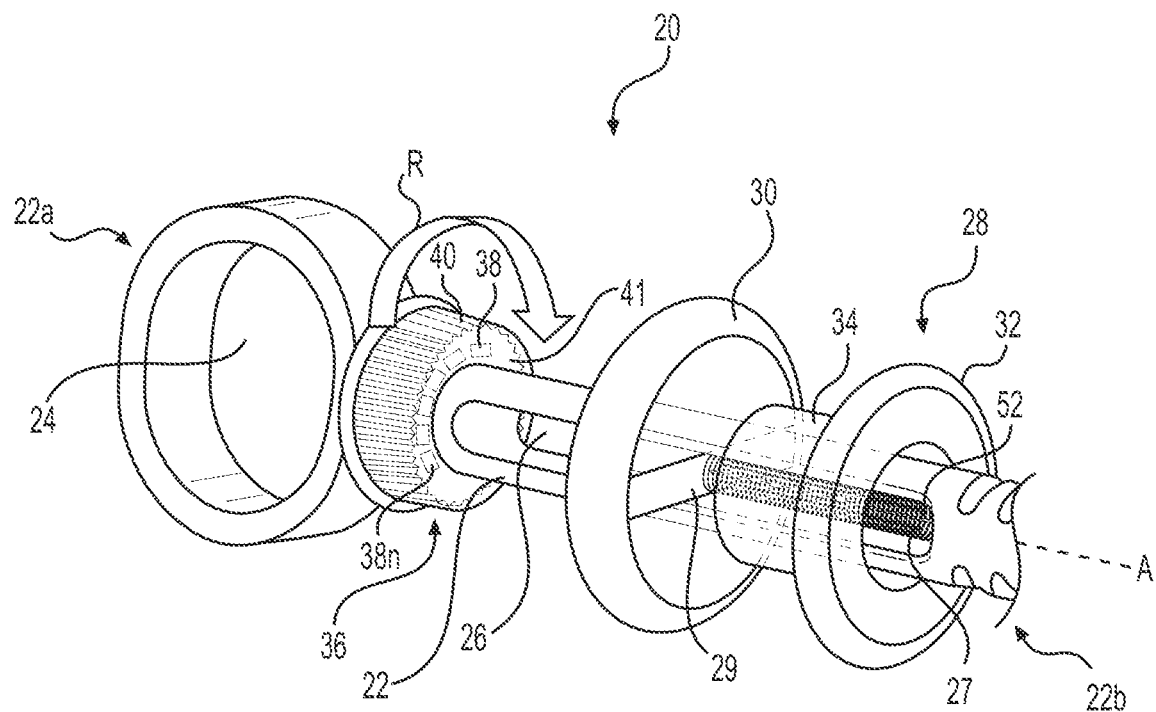
FIG. 2 is a perspective view of a handle of the medical device of FIG. 1.

With reference to FIG. 2, a ratchet 36 is circumferentially disposed around body 22 and between hole 24 and slot 26, proximal of spool 28. A plurality of cavities 38 are circumferentially arranged on ratchet 36, each cavity being parallel to longitudinal axis A and facing distal end 22b of handle 22 (it will be understood that there may be a single cavity 38 shaped as cavity 38n, which would be useful for a single-use medical device 10). According to an example, medical device 10 includes six cavities 38, but is not limited to this number of cavities 38. The number of cavities 38 may be limited by the amount of dispensable devices 60 to be dispensed by medical device 10, e.g., any number of dispensable devices 60 may be pre-loaded in medical device 10 for a single procedure. As shown in FIG. 2, cavities 38 are generally rectangular in shape, but may be any shape suitable for achieving the ratchet movement described herein. Ratchet 36 may further include a plurality of ridge-like protrusions 40 extending from a side surface, e.g., circumferentially around, and perpendicular to longitudinal axis A. Protrusions 40 may provide a textured feel and/or may aid in operability of ratchet 36 by providing a location for a user to grasp. Ratchet 36 is rotatable about axis A relative to body 22.

Figure 3:
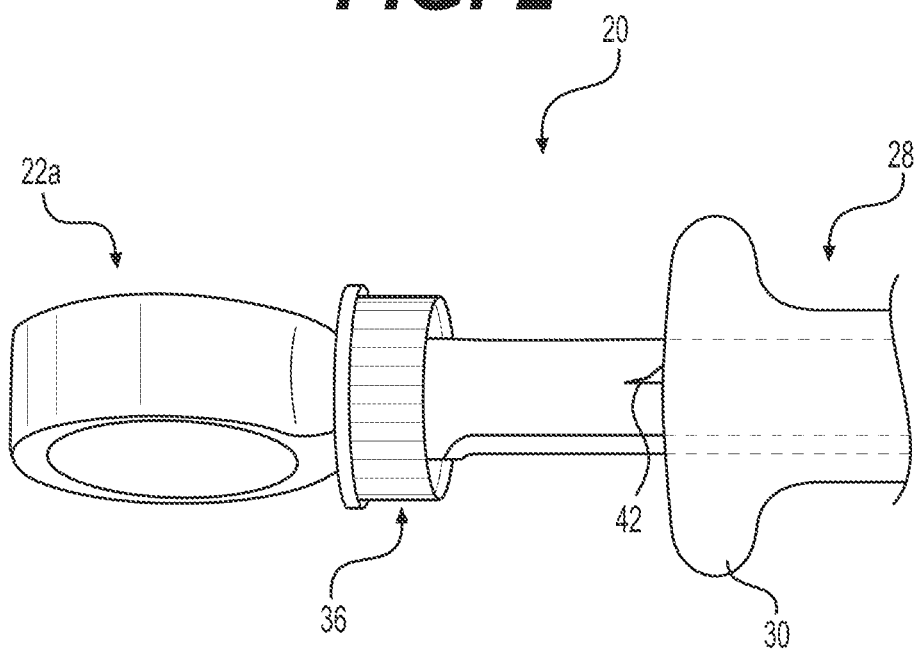
FIG. 3 is another perspective view of the handle of FIG. 2.

With reference to FIG. 3, a protrusion 42 extends in a proximal direction from the proximalmost annular protrusion 30 of spool 28. A wall of protrusion 42 is angled relative to axis A, e.g., with a ramp shape, and sized and shaped to be received within cavities 38. As will be discussed in greater detail below, protrusion 42 interacts with cavities 38 and operates ratchet 36, e.g., to rotate about body 22 in a direction indicated by arrow R (clockwise in the view of FIG. 2).

Figure 4:
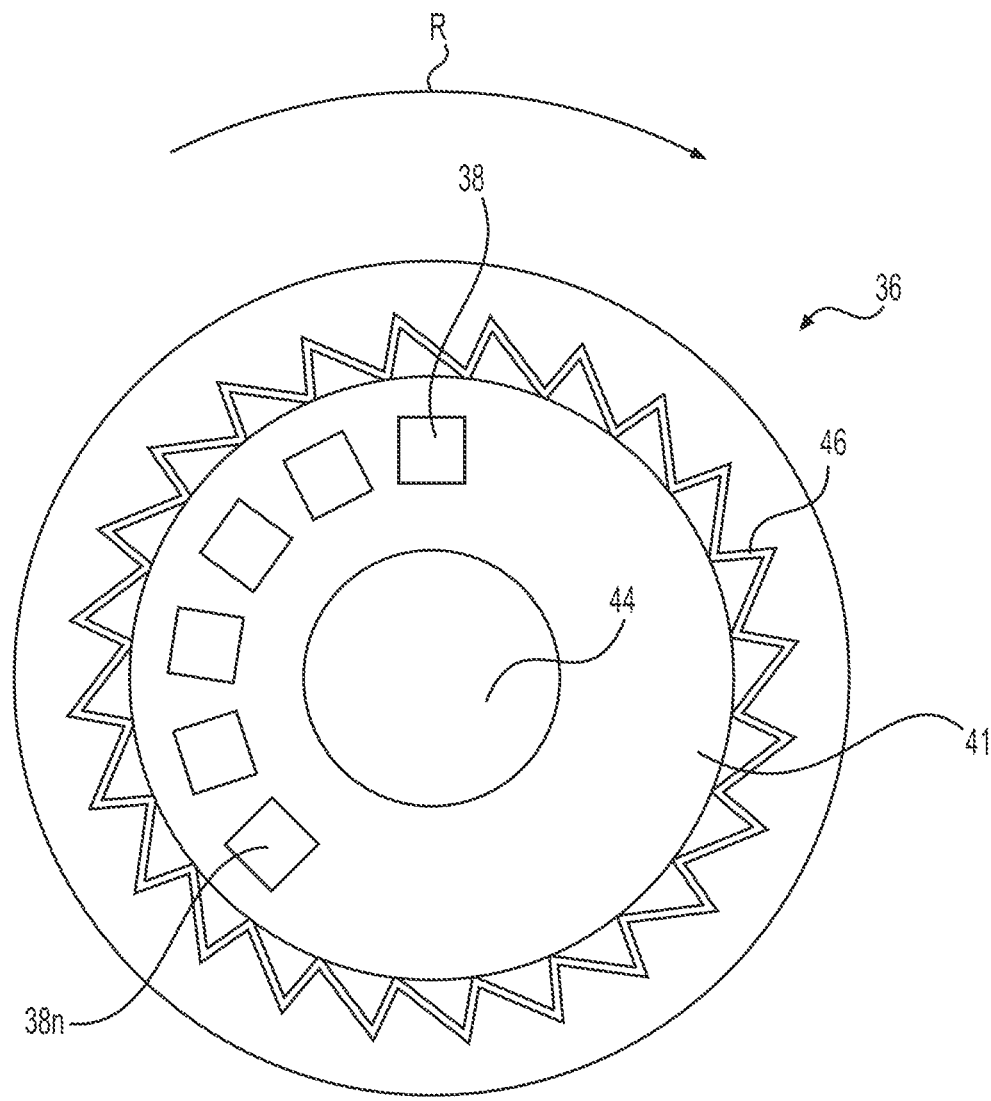
FIG. 4 is an end view of a ratchet of the medical device of FIG. 1.

Ratchet 36 and cavities 38 are shown in greater detail in FIGS. 4 and 5A-5C. With reference to FIG. 4, a distal end of ratchet 36 is shown and includes a distal face 41 defining cavities 38. Throughhole 44 extends from the distal end of ratchet 36 to a proximal end thereof. Body 22 extends through throughhole 44 and allows ratchet 36 to rotate about body 22. Teeth 46 are provided on an inner circumferential surface of ratchet 36, between proximal and distal ends of ratchet 36, and angled in a rotation direction, e.g., as indicated by arrow R in FIGS. 2 and 3. Teeth 46 may prevent ratchet 36 from rotating in a direction opposite rotation direction R by grasping a stop piece (not shown) of handle 20. The stop piece will engage a tooth 46 as ratchet 36 rotates, allowing ratchet 36 to rotate to a next one of the cavities 38 and preventing opposite rotation.

Figure 5A:
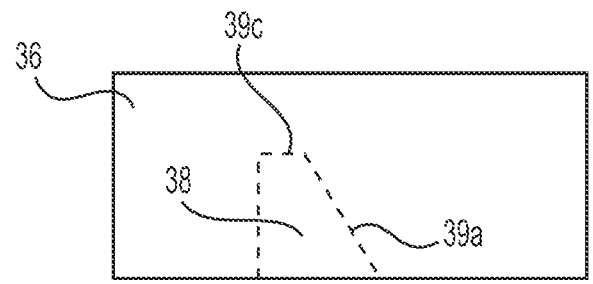
FIGS. 5A-5C are side views of the ratchet of FIG. 4 and a spool of the medical device of FIG. 1.
Figure 5B:
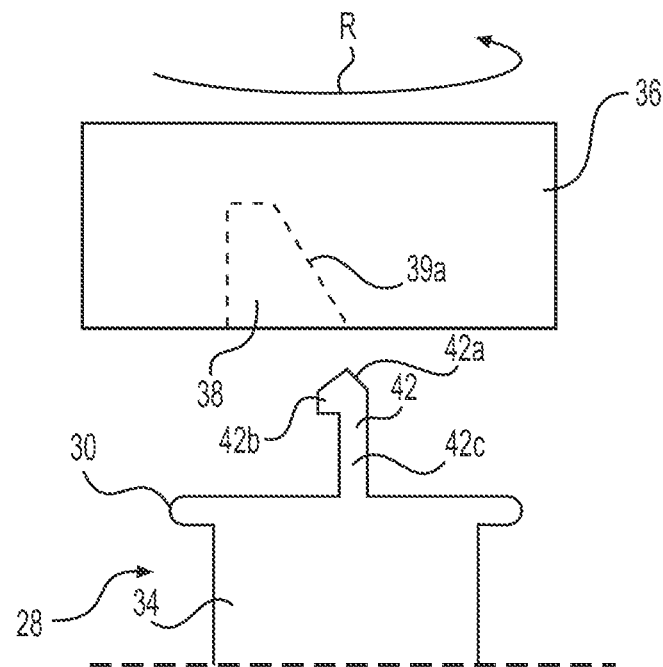
Figure 5C:
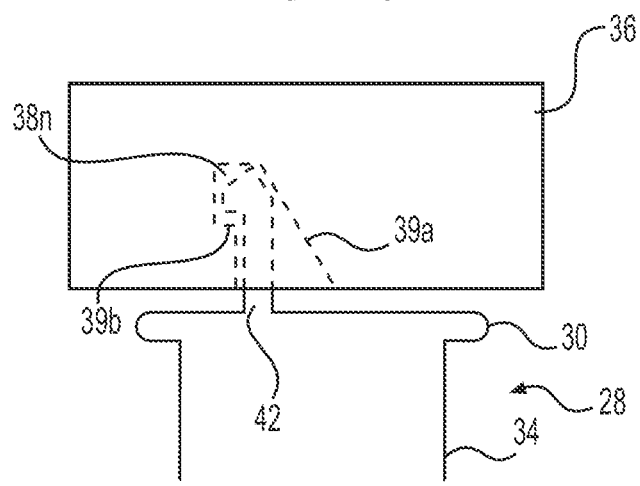

With reference to FIGS. 5A-5C, a side view of ratchet 36 is illustrated with cavities 38. As shown in FIG. 5A, cavity 38 includes a ramp 39a on a side of cavity 38 in the direction of rotation R. Ramp 39a is angled in relation to axis A so that the inside distally facing wall 39c of cavity 38 is smaller than the opening to cavity 38. FIG. 5B shows protrusion 42 on spool 28. Protrusion 42 may be inserted into an individual cavity 38 and slide along ramp 39a, causing ratchet 36 to rotate in the rotation direction R around handle 20. As this occurs, a tooth 46 disengages from a stop-piece in body 22, and an adjacent tooth 46 engages the stop-piece. A topmost portion of protrusion 42 may have an angled surface 42a with a slope similar to the slope of ramp 39a, aiding to rotate ratchet 36 in the rotation direction R. Protrusion 42 includes a flanged portion 42b extending from an arm 42c of protrusion 42, in a direction opposite to rotation direction R. As devices 60 are deployed, protrusion 42 may sequentially, or individually, engage with each cavity 38, until protrusion 42 enters the final cavity 38n.

As shown in FIG. 5C, a final cavity 38n from among the plurality of cavities 38 is shaped differently from the other cavities 38. Protrusion 42 may slide along ramp 39a of final cavity 38n. Flanged portion 42b of protrusion 42 may interact with a surface 39b of final cavity 38n, which is substantially perpendicular to an insertion direction of protrusion 42. For example, flanged portion 42b engages surface 39b, preventing protrusion 42 and spool 28 from moving distally, thereby locking ratchet 36 and spool 28 together.

Figure 6:
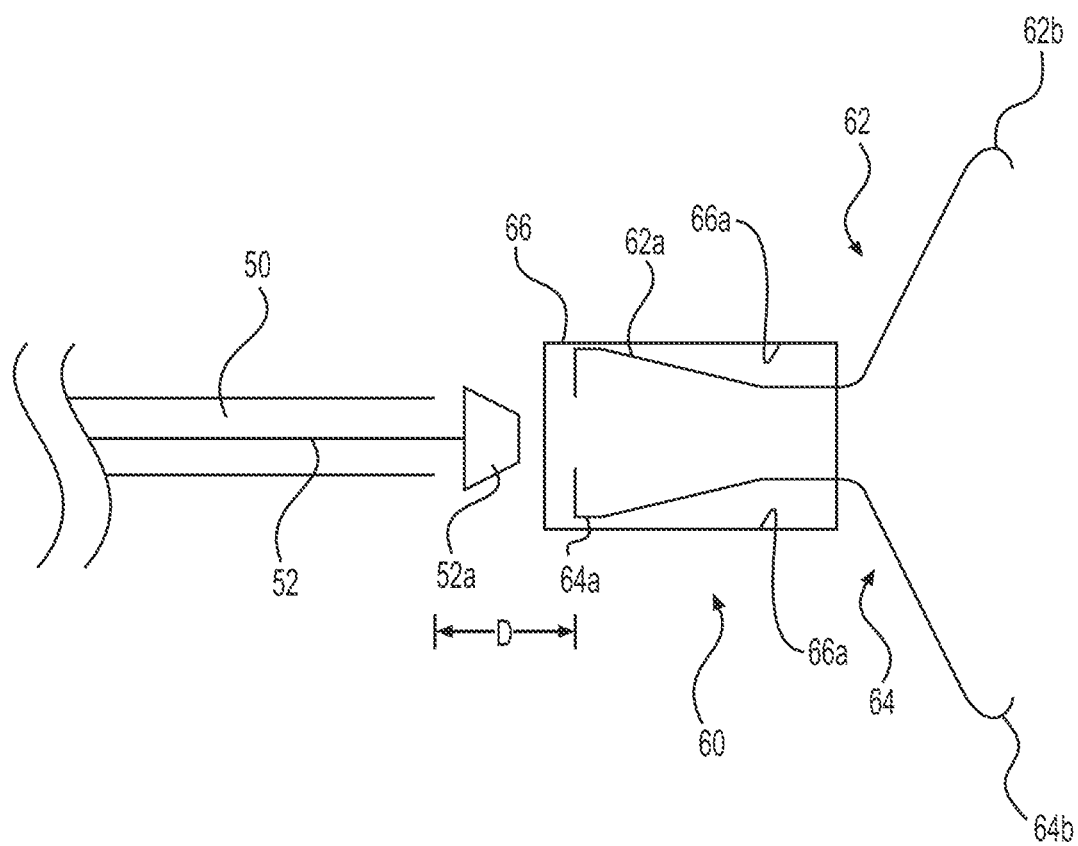
FIG. 6 is a side view of a catheter and dispensable device according to an exemplary embodiment.

With reference to FIG. 6, dispensable device 60 is shown. According to an embodiment, device 60 is a tissue clip for clipping tissue together. However, it will be understood that device 60 is not limited to this configuration, and may include any tool, device, or material that may be dispensed into a patient, such as any multiple use devices intended for single patient use including, but not limited to, snares, graspers, biopsy forceps, or the like, thereby preventing multiple use devices from being used in multiple patients. According to an example, device 60 includes a body 66 at a proximal end of device 60. A pair of jaws, hooks, or prongs 62, 64 extend distally from body 66, and hooks 62, 64 include proximal ends 62a, 64a and distal ends 62b, 64b, respectively. Device 60 may be attached to a distal end of wire 52 via a connection between a distal element 52a of wire 52 and proximal ends 62a, 64a. According to an embodiment, distal end 52a must travel at least a predetermined distance D past a distalmost end of catheter 50 to load device 60 onto medical device 10. For example, predetermined distance D is a distance necessary for distal end 52a to extend past the distalmost end of catheter 50 to enter a proximal end of body 66 and engage or otherwise grasp proximal ends 62a, 64a of hooks 62, 64. As will be described in greater detail herein, once device 60 is loaded on distal end 52a, device 60 may grasp tissue by pulling proximally on spool 28, thereby causing wire 52, distal end 52a, and proximal ends 62a, 64a to travel proximally. As proximal ends 62a, 64a are drawn proximal of body 66, distal ends 62b, 64b approach each other and close about tissue (not shown) therebetween. Distal ends 62b, 64b close together as an inner distal surface 66a of body 66 engages outer surfaces of arms 62, 64, as arms 62, 64 are pulled into body 66. Once proximal ends 62a, 64a are drawn proximally a sufficient amount, proximal ends 62a, 64a will separate and release distal end 52a, so that device 60 is released from medical device 10. In some embodiments, arms 62, 64 may be biased in a closed configuration, although in other embodiments, the arms 62, 64 may be biased in an open configuration.

Figure 7:
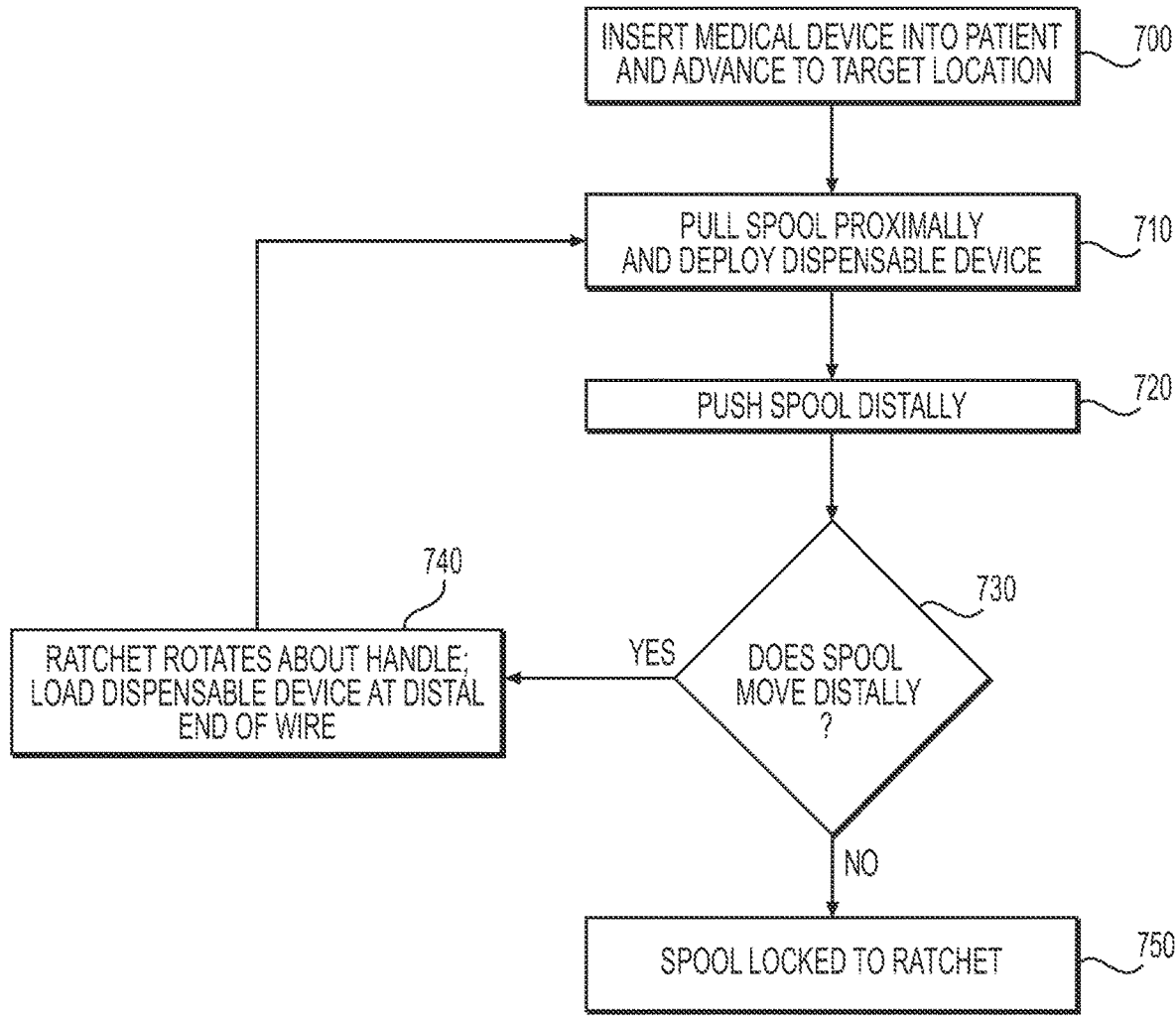
FIG. 7 is a method of dispensing a device from the medical device of FIG. 1.
Figure 9:
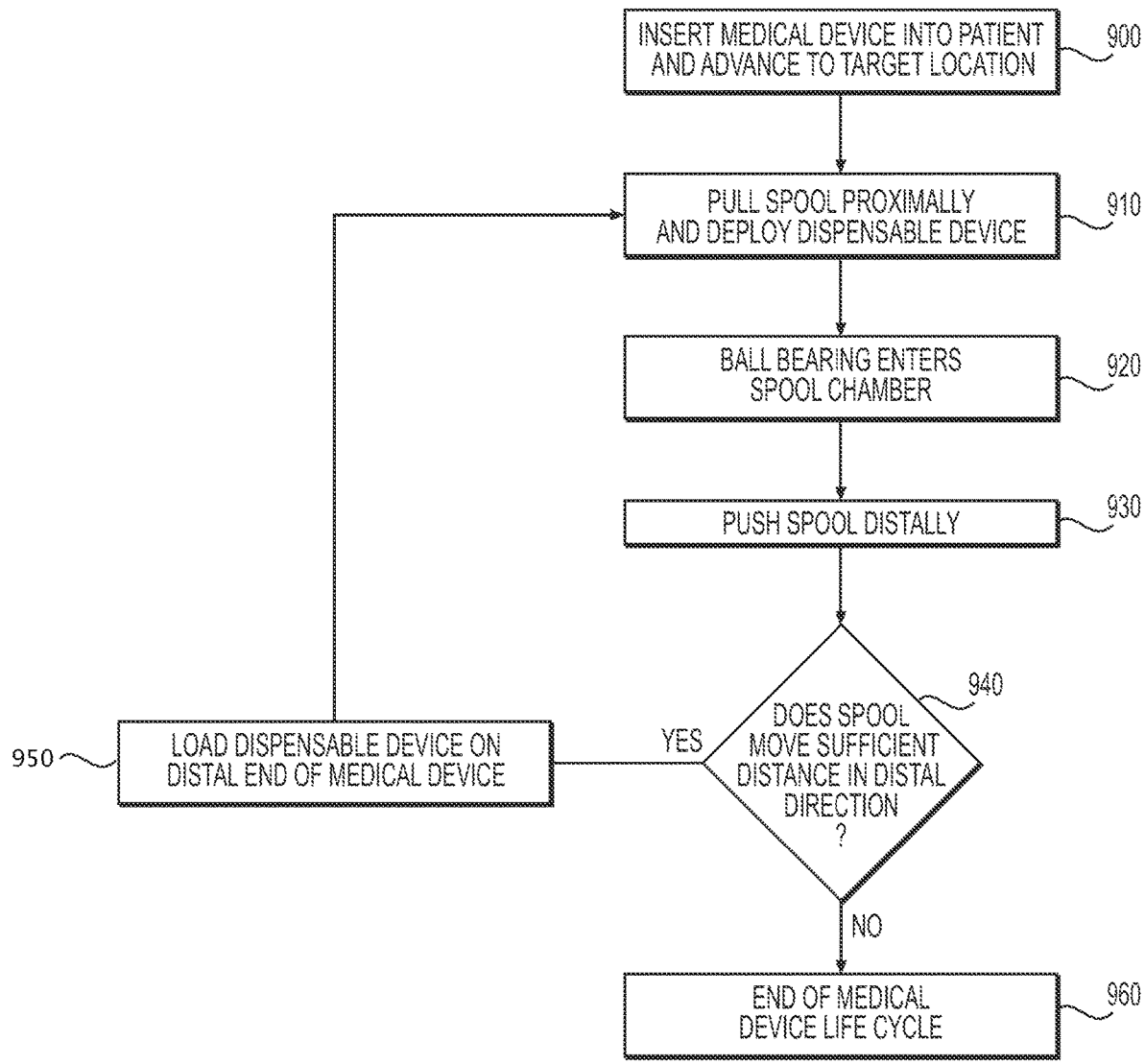
FIG. 9 is a method of dispensing a device from the medical device of FIGS. 8A-8C.

A method of operation of medical device 10 will now be described with reference to FIG. 7. Referring to Step 700, a distal end of medical device 10, including dispensable device 60, is introduced into a patient and advanced to a desired location. The desired location may be, e.g., a location for dispensing device 60, such as a clip for joining two or more adjacent tissues together (see, e.g., FIG. 6). Once device 60 is at the desired location, device 60 is deployed in Step 710. In Step 710, a user grasps spool 28 around annular grip 34 and the user pulls spool 28 proximally relative to body 22 to deploy device 60. When spool 28 reaches a proximalmost end of slot 26, protrusion 42 enters a first cavity 38 from among the plurality of cavities 38. In Step 720, the user pushes spool 28 distally, if the user wishes to load another dispensable device 60. In Step 730, it is determined if spool 28 does indeed move distally and if protrusion 42 exits cavity 38. If spool 28 moves distally, protrusion 42 exits cavity 38 and causes ratchet 36 to rotate about body 22. Another device 60 is then loaded on wire 52 in Step 740. According to an example, ratchet 36 rotates around body 22 of handle 20 in the direction of arrow R, e.g., in a clockwise direction. However, ratchet 36 may rotate counterclockwise around body 22, if cavities 38 and teeth 46 are arranged differently, in another embodiment. Once protrusion 42 exits cavity 38, spool 28 may again be pushed distally to deploy a next device 60 in Step 710. It will be understood, however, that deployment of devices 60 may be terminated if a physician has no further need to deploy devices 60. If it is determined that spool 28 does not move distally in Step 730, spool 28 is locked in place by the interaction of protrusion 42 and cavity 38n in Step 750, such that no additional device 60 may be loaded on distal end 52a of wire 52. The locking of spool 28 against ratchet 36 prevents reuse of medical device 10 once all devices 60 are deployed.

In another embodiment, medical device 110 is illustrated in FIGS. 8A-8C. Medical device 110 includes similar features as medical device 10, including catheter 50 and device 60 attachable to a distal end thereof. A handle 120 is attached to a proximal end of catheter 50. Handle 120 includes some features similar to those of handle 20, and these features are illustrated with like reference numerals. Handle 120 further includes a tube 121 defining chamber 122 adjacent and parallel to body 22. Chamber 122 generally extends a same distance, or substantially a same distance, as slot 26, but is not limited to this size. Chamber 122 includes a plurality of ball bearings 124 (it will be understood that there may be a single cavity ball bearing 124, which would be useful for a single-use medical device 110). According to an example, medical device 110 includes six ball bearings 124, but is not limited to this number of ball bearings. The number of ball bearings may be limited by the amount of dispensable devices 60 to be dispensed by medical device 110. Tube 121 includes a retention device 126, and a magnet 125 disposed at a distal end of chamber 122. As will be described in greater detail, ball bearings 124 are initially disposed at a proximal end of chamber 122 and held in position by retention device 126, which may be a portion of the wall of tube 121 having a smaller inner diameter than a remainder of the wall of tube 121, so that the wall 121 imparts a friction force on bearing 124. That force helps retain bearings 124 in position until subject to a sufficient force that overcomes the friction force, allowing release of bearings 124. Ball bearings 124 may be any material having a magnetic property, for the reasons set forth below. It will also be understood that only a portion of ball bearings 124 may include magnetic material, such as a center or a covering of ball bearing 124, and/or ball bearing 124 may be any other shape.

With continued reference to FIGS. 8A-8C, a spool 128 surrounds a circumference of handle 120 and chamber 122. Spool 128 includes a fixing member 130 (similar to bar 29 in FIG. 2) slidably received in slot 26 and which allows spool 128 to slide proximally and distally along handle 120 and chamber 122. According to an example, a proximalmost end of wire 52 is attached to fixing member 130. It will be understood, however, that wire 52 may be attached to another portion of spool 128. Spool further includes a spool chamber 132 slidably received in chamber 122. As shown in FIG. 8A, a proximal end of spool chamber 132 includes tapered walls 136 so that chamber 132 has a smaller inner diameter at the proximal tapered portion. The tapered portion of the wall 136 may be flexible to allow entry of ball bearing 124 upon a sufficient force applied to bearing 124. A distal end of spool chamber 132 includes a one-way gate 134 rotatable about a gate axis G, as shown by arrow O in FIG. 8A. While gate axis G is shown adjacent to body 22 of handle 120, it will be understood that gate axis G is not limited to this position and may be, e.g., positioned on an outermost edge of chamber 122. Gate 134 may be a magnet and/or may include a magnet to attract ball bearing 124. The strength of the magnet on or in gate 134 is less than the strength of magnet 125.

Similar to handle 20, spool 128 of handle 120 dispenses device 60 when pulled in a proximal direction and loads a next device 60 when pushed in the distal direction. As spool 128 approaches the proximal end of handle 120, magnetic gate 134 attracts the distalmost ball bearing 124a and allows the distalmost ball bearing 124a into spool chamber 132. The magnetic force overcomes the friction force retaining bearing 124 in chamber 122, and applies a sufficient force to overcome any force applied by tapered wall 136. When spool 128 is positioned at the distal end of handle 120, ball bearing 124a is magnetically attracted to magnet 125, causing gate 134 to rotate about gate axis G to open (as shown in FIG. 8C) and deposit ball bearing 124a at magnet 125. In the event gate 134 is magnetized, magnet 125 has magnetic force sufficient to overcome the magnetic force of gate 134. Proximal movement of spool 128 allows gate 134 to close once gate 134 is free of the deposited ball bearing 124. As will be explained in detail below, ball bearings 124 may be sequentially or individually moved from the proximal end of chamber 122 to the distal end of chamber 122. Magnet 125 has a sufficient magnetic force to pull a final ball bearing 124n through gate 134. Once all of bearings 124 to 124n have been deposited at the distal end of chamber 122, spool 128 cannot be advanced distally sufficiently to allow loading of another dispensable device 60, such as a clip, e.g., ball bearings 124 act as a spacer to prevent subsequent deployment of additional devices 60.

A method of operation of medical device 110 illustrated in FIGS. 8A-8C will now be described. In Step 900, a distal end of medical device 110, including device 60, is introduced into a patient and advanced to a desired location. As with the method described in FIG. 7, the desired location may be, e.g., a location for dispensing device 60, such as a clip for joining two or more adjacent tissues together. Once device 60 is at the desired location, device 60 is deployed. In Step 910, a user grasps spool 128 around annular grip 34 and user pulls spool 128 proximally to deploy device 60. As spool 128 reaches a proximal end of handle 120, a distalmost ball bearing 124a enters spool chamber 132 in Step 920. As discussed above, distalmost ball bearing 124a is disposed in spool chamber 132, magnetically attracted to a proximal side of gate 134. In Step 930, the user pushes spool 128 distally to begin the process of loading another dispensable device 60. In Step 940, it is determined if spool 128 moves distally at least distance D to load a next device 60 on wire 52. If spool 128 moves distance D in a distal direction, next device 60 is loaded at distal end 52a of wire 52 in Step 950. If a last ball bearing 124n has been deposited at the distal end of chamber 122, however, spool 128 will be unable to move the sufficient distance to load a device 60, and it will be determined in Step 960 that medical device 110 is unable to accept an additional device 60, thereby preventing the reuse of medical device 110.

It will be understood that handle 20, and other parts of medical devices 10, 110, may be made of any material known in the art, including, but not limited to, a medical grade plastic or rubber, a ceramic, a metal, or a combination thereof.

It will be apparent to those skilled in the art that various modifications and variations can be made to the disclosed device without departing from the scope of the disclosure. For example, the medical device may be used to dispense and/or prevent loading of medial clips or other similar devices. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical device, comprising:
   a handle body having a proximal end and a distal end;
   a handle portion on the handle body and configured to move relative to the handle body;
   a catheter extending from the distal end of the handle body;
   a wire attached to the handle portion and extending through the catheter, wherein the wire is configured to be removably connected to a dispensable device at a distal end of the catheter such that movement of the handle portion relative to the handle body actuates the wire to release the dispensable device; and
   a controller to prevent connection of another dispensable device to the wire after the dispensable device has been dispensed by the medical device, wherein the controller includes:
      a first chamber extending along the handle body, wherein a plurality of elements are disposed within the first chamber, wherein the plurality of elements are configured to be moved sequentially and individually from a proximal end of the first chamber to a distal end of the first chamber; and
      a second chamber defined by the handle portion, wherein the second chamber is movable within the first chamber.

2. The medical device of claim 1, wherein the first chamber includes a retention device at the proximal end of the first chamber, and the plurality of elements are initially disposed within the retention device.

3. The medical device of claim 1, wherein the second chamber releases a distalmost element from the plurality of elements at the proximal end of the first chamber and moves the distalmost element toward the distal end of the first chamber.

4. The medical device of claim 1, wherein the first chamber further includes a magnet at a distal end, and a magnetic force of the magnet is configured to pull at least one of the plurality of elements from the second chamber toward the distal end of the first chamber.

5. The medical device of claim 1, wherein a distal end of the wire extends at least a predetermined distance from a distalmost end of the catheter to connect to the another dispensable device, and
   the connection of the distal end of the wire to the another dispensable device is prevented when one or more of the plurality of elements moved from the proximal end of the first chamber to the distal end of the first chamber extend a distance from the distal end of first chamber that is greater than the predetermined distance.

6. The medical device of claim 1, wherein the handle portion includes a spool, and the spool comprises:
   a first annular protrusion at a proximal end of the handle portion;
   a second annular protrusion at a distal end of the handle portion; and
   an annular grip defined by the first annular protrusion and the second annular protrusion, the annular grip configured to be grasped by an operator of the medical device to move the handle portion relative to the handle body.

7. The medical device of claim 2, wherein the retention device is a first portion of the first chamber having a smaller inner diameter than a remaining second portion of the first chamber.

8. The medical device of claim 3, wherein a distal end of the second chamber includes a gate, and wherein the gate is biased in a closed configuration closing the distal end of the second chamber.

9. The medical device of claim 3, wherein the second chamber releases the distalmost element into the second chamber, and wherein a proximal end of the second chamber configured to receive the distalmost element is tapered.

10. The medical device of claim 8, wherein the gate includes a magnet, the distalmost element has a magnetic property, and a magnetic force of the magnet is configured to release the distalmost element.

11. The medical device of claim 4, wherein a distal end of the second chamber includes a gate, wherein the gate is biased in a closed configuration closing the distal end of the second chamber, and wherein the magnet overcomes a bias of the gate to pull the at least one of the plurality of elements through the gate toward the magnet.

12. The medical device of claim 4, wherein at least a portion of each of the plurality of elements includes material having a magnetic property.

13. The medical device of claim 11, wherein when the magnet overcomes the bias of the gate, the gate is rotatable about a gate axis to open the distal end of the second chamber.

14. A medical device, comprising:
   a handle body having a distal end, a proximal end, and a first chamber extending along a length of the handle body;
   a handle portion on the handle body and movable between the distal end and the proximal end of the handle body, wherein the handle portion includes a second chamber movable within the first chamber;
   a catheter extending from the distal end of the handle body; and
   an actuator attached to the handle portion and extending through the catheter, wherein the actuator is configured to be removably connected to a first dispensable device at a distal end of the catheter;
   wherein the first chamber includes at least one element, and the medical device prevents loading of a second dispensable device when the at least one element is disposed at a distal end of the first chamber,
   wherein a distal end of the actuator extends at least a predetermined distance from a distalmost end of the catheter to attach to the second dispensable device, and
   wherein, when the at least one element is disposed at the distal end of the first chamber, the at least one element extends a distance from the distal end of the first chamber that is greater than the predetermined distance.

15. A medical device, comprising:
   a handle body having a proximal end, a distal end, and a first chamber, wherein the first chamber extends along a length of the handle body and includes an element initially disposed at a proximal end of the first chamber;
   a handle portion on the handle body and movable relative to the handle body, wherein the handle portion includes a second chamber movable within the first chamber;
   a catheter extending from the distal end of the handle body; and
   an actuator attached to the handle portion and extending through the catheter, wherein the actuator is configured to be removably connected to a dispensable device at a distal end of the catheter;
   wherein, after the actuator is connected to the dispensable device and as the handle portion is moved relative to the handle body to dispense the dispensable device, the second chamber is configured to release the element initially disposed at the proximal end of the first chamber; and
   wherein, as the handle portion is moved relative to the handle body to load another dispensable device, the second chamber is configured to move the element toward the distal end of the first chamber.

16. The medical device of claim 15, wherein a distal end of the actuator extends at least a predetermined distance from a distalmost end of the catheter to attach to the another dispensable device, and
   the medical device prevents the loading of the another dispensable device when the element extends a distance from the distal end of the first chamber that is greater than the predetermined distance.

17. The medical device of claim 15, wherein a distal end of the actuator extends at least a predetermined distance from a distalmost end of the catheter to attach to the another dispensable device, and
   the distal end of the actuator is attached to the another dispensable device when the element extends a distance from the distal end of the first chamber that is less than the predetermined distance.

* * * * *